(12) United States Patent
Lentz

(10) Patent No.: US 7,727,187 B2
(45) Date of Patent: Jun. 1, 2010

(54) SCORED CATHETER DEVICE

(75) Inventor: David Christian Lentz, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 769 days.

(21) Appl. No.: 11/396,850

(22) Filed: Apr. 3, 2006

(65) Prior Publication Data

US 2006/0224112 A1 Oct. 5, 2006

Related U.S. Application Data

(60) Provisional application No. 60/668,197, filed on Apr. 4, 2005.

(51) Int. Cl.
*A61M 29/00* (2006.01)
(52) U.S. Cl. .............................. 604/103.04; 604/96.01; 604/103; 604/525; 623/1.11
(58) Field of Classification Search .............. 604/96.01, 604/103, 103.04, 525; 623/1.11
See application file for complete search history.

(56) References Cited

U.S. PATENT DOCUMENTS

| 4,362,150 | A | * | 12/1982 | Lombardi et al. ............. 600/18 |
| 4,762,129 | A |   | 8/1988  | Bonzel |
| 4,960,410 | A | * | 10/1990 | Pinchuk ................... 604/96.01 |
| 5,425,711 | A |   | 6/1995  | Ressemann et al. |
| 5,507,768 | A |   | 4/1996  | Lau et al. |
| 5,690,644 | A |   | 11/1997 | Yurek et al. |
| 5,728,067 | A |   | 3/1998  | Enger |
| 5,795,325 | A | * | 8/1998  | Valley et al. ................. 604/509 |
| 6,346,092 | B1| * | 2/2002  | Leschinsky ............... 604/96.01 |
| 6,648,854 | B1| * | 11/2003 | Patterson et al. ......... 604/96.01 |
| 2003/0105427 | A1 | * | 6/2003 | Lee et al. ............... 604/103.04 |
| 2004/0133158 | A1 |   | 7/2004 | Keith et al. |
| 2005/0283221 | A1 | * | 12/2005 | Mann et al. ................ 623/1.11 |

FOREIGN PATENT DOCUMENTS

EP 01 374 943 A1 1/2004

OTHER PUBLICATIONS

Meredith, Ian T., Driver® Stent Experience, Dec. 2003, 18 pages.
Creganna Medical Devices, brochure, 2004, 14 pages.

* cited by examiner

*Primary Examiner*—Nicholas D Lucchesi
*Assistant Examiner*—Laura A Bouchelle
(74) *Attorney, Agent, or Firm*—Brinks Hofer Gilson & Lione

(57) ABSTRACT

A catheter device including an elongate tubular shaft having a consistent material composition for a substantial proportion of its length. The device includes a proximal shaft portion having a first flexibility and a distal shaft portion having a second flexibility, wherein the second flexibility is greater than the first flexibility and wherein at least the distal shaft portion comprises at least one score in a surface thereof.

13 Claims, 7 Drawing Sheets

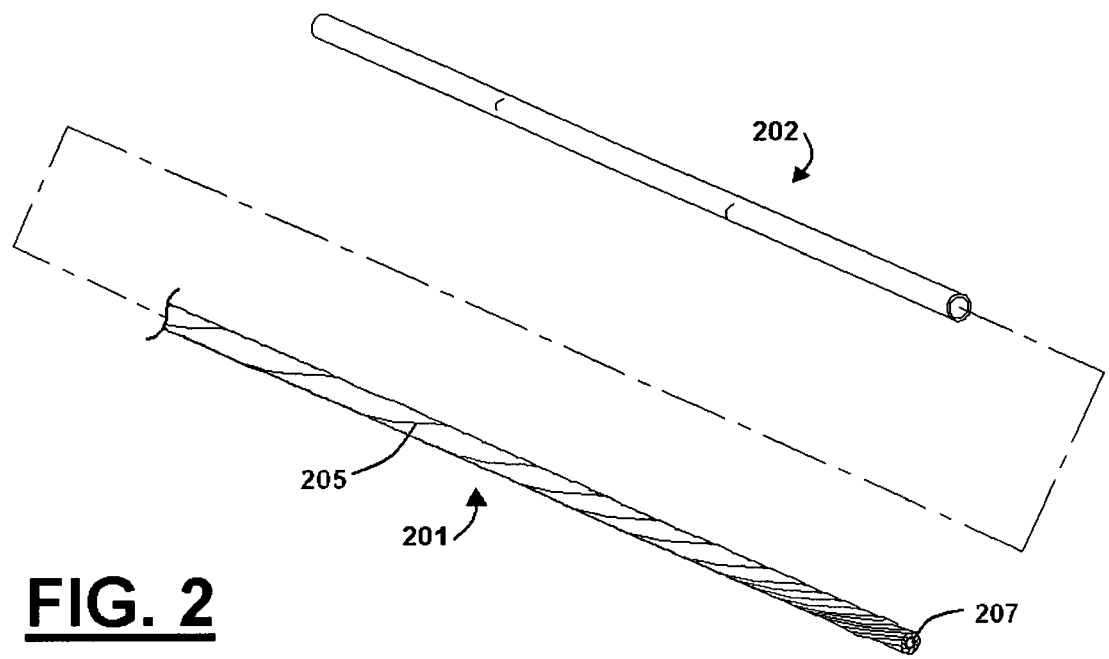
FIG. 2
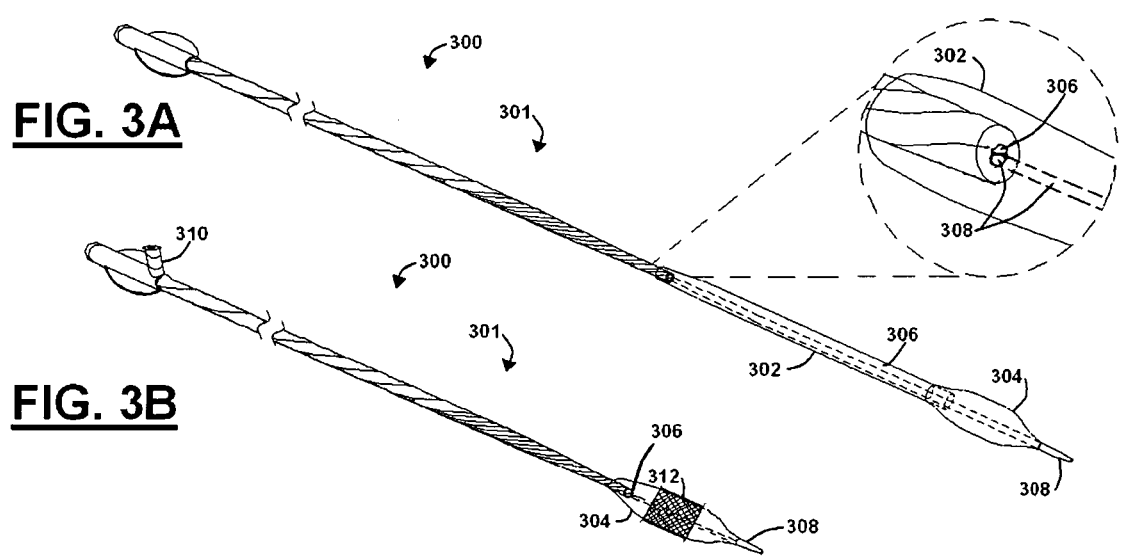
FIG. 3A
FIG. 3B

SCORED CATHETER DEVICE

CROSS-REFERENCE TO RELATED APPLICATIONS

This application claims priority to U.S. Provisional Application Ser. No. 60/668,197, filed Apr. 4, 2005, which is incorporated herein by reference in its entirety.

FIELD OF INVENTION

The present application relates to medical catheters, and more specifically to medical catheters useful in endovascular, biliary, and other body lumens.

BACKGROUND

Medical delivery catheters are well known in the art of minimally invasive surgery for introduction of fluids and devices to sites inside a patient's body. For example, balloon dilation of luminal stenoses (e.g., in procedures such as angioplasty or balloon dilation of a bile duct), stent placement, and introduction of radio-opaque contrast fluids are common uses of catheters.

The most widely used form of angioplasty makes use of a dilation catheter having an inflatable balloon at its distal end. In coronary procedures, a hollow guide catheter or wire guide typically is used for guiding the dilation catheter through the vascular system to a position near the stenosis (e.g., to a coronary arterial lumen occluded by plaque). Using fluoroscopy, the physician guides the dilation catheter the remaining distance through the vascular system until a balloon is positioned to cross the stenosis. The balloon is then inflated by supplying pressurized fluid, through an inflation lumen in the catheter, to the balloon. Inflation of the balloon causes a widening of the lumen of the artery to reestablish acceptable blood flow through the artery. In some cases, a stent may be deployed with or instead of the balloon to widen and hold open the occluded arterial lumen.

Preferably a catheter used in endovascular lumens will have several physical characteristics. The profile and shaft size of the dilation catheter should be such that the catheter can reach and cross a very tight stenosis. Portions of the dilation catheter must also be sufficiently flexible to pass through a tight curvature or tortuous passageway, especially in a catheter adapted for use in the coronary arteries. The ability of a catheter to bend and advance effectively through the endovascular or other lumens is commonly referred to as the "trackability of the catheter." Another important feature of a dilation catheter is its "pushability." Pushability involves the transmission of longitudinal forces along the catheter from its proximal end to its distal end so that a physician can push the catheter through the vascular or other lumenal system and the stenoses. Effective catheters should be both trackable and pushable.

Two commonly used types of dilation catheters are referred to as "long-wire" catheters and "short-wire" catheters. A long-wire catheter is one in which a wire guide lumen is provided through the length of the catheter that is adapted for use with a wire guide that can first be used to establish the path to and through a stenosis to be dilated. The dilation catheter can then be advanced over the wire guide until the balloon on the catheter is positioned within the stenosis.

In short-wire catheters, the wire guide lumen does not extend the entire length of the catheter. In this type of catheter, the wire guide lumen extends only from the distal end of the balloon to a point intermediate the distal and proximal ends of the catheter. This shorter lumen is the only internal portion of the catheter contacting the wire guide. It is sometimes desirable to exchange this first catheter and/or balloon for a second catheter (e.g., to "exchange out" a balloon catheter, and then "exchange in" a stent-deployment catheter). The exchange is preferably executed by leaving the wire guide in place during removal of the first catheter and using it as a guide for the second catheter. The first catheter is withdrawn or otherwise removed over the wire guide, and then a second catheter is introduced over the wire guide.

Short-wire catheters are often easier to exchange than catheters having the wire guide lumen extending the entire length of the catheter. In part, this is because the wire guide need not be as long as a "long wire" configuration, which requires that a length of the wire guide extending outside the patient's body be longer than the portion of the catheter extending over the long wire guide in order for a doctor or assistant to maintain a grasp on the wire guide (to avoid undesired movement or displacement thereof). The short wire guide configuration catheters also create less friction during mounting and exchange operations due to the shorter wire guide lumen, leading to a reduced likelihood of displacing the wire guide.

Catheters for use in endovascular lumens typically require a variation in physical properties along different portions thereof. For example, a certain degree of stiffness is required for pushability and trackability near the proximal end while the distal end requires a great deal of flexibility. A catheter having uniform properties throughout its length may pose disadvantages in that it is likely to be too proximally flexible or too distally stiff. As a result, most catheter shafts (especially endovascular catheters) are made from multiple materials along the shaft length. For example, a catheter shaft may have a stiff proximal portion made of hypotube, a middle portion made of a stiff plastic, and a distal portion made of a more flexible plastic. This combination of materials poses problems of cost and efficiency in construction, and the junctions provide problematic possibilities for structural failure (such as binding, kinking, or even separation) as well as requiring specialized connection means.

In another example, a catheter shaft may be made of plastic for a major part of its length, but have a stiffening wire disposed through a significant portion of that length to enhance stiffness. Some long wire catheters rely almost wholly on placement of a wire guide therethrough to retain the needed stiffness, which presents the problems of length and unwieldiness discussed above. In contrast, the proximal sections of short wire catheters must have adequate stiffness independent of the wire guide.

Several different structures for shortened guide wire lumen dilation catheters have been proposed and used to obtain the desired physical properties described above, but each of these structures tends to suffer from several disadvantages. For example, in a short wire catheter having a relatively flexible one-piece plastic design, because only a small portion of the wire guide extends through the catheter body near the distal end of the catheter shaft, the wire guide portion does not contribute to the pushability of the rest of the catheter shaft. As a result, the proximal shaft portion of such a catheter has low column strength. With such a configuration, the shaft and/or guide wire may tend to develop undesirable flexure (e.g., scissoring, bowing, buckling, kinking) when the balloon is being manipulated in a lumen. This undesired flexure may cause an irregular exterior surface such as a sharp edge which can in turn cause injurious abrasions to the inner lining of the artery or other lumen (e.g. other body lumen or a working lumen of an endoscope). This undesired flexure can also lead to poor pushability and trackability of the catheter.

To counteract this deficiency, some known designs have extended the length of the wire guide lumen and/or provided additional stiffener elements in the shaft.

In one design, a significant proximal portion of the catheter shaft is made of a metallic tubing (commonly referred to as a hypotube), which provides the desired pushability while maintaining a relatively small outer diameter. The distal portion of the catheter shaft is a second, more flexible (commonly plastic) tubing. In short-wire catheters using the hypotube design, a first aperture for passage of a wire guide from/to the wire guide lumen is usually placed in the hypotube near to the distal end thereof. Alternatively, this first aperture is placed in the second tubing, or near the juncture between the hypotube portion and the second tubing. These types of catheters, however, present certain disadvantages. Having the first aperture in the hypotube portion mitigates the advantages of a short-wire catheter: the wire guide must be longer, and advantages conferred by reduced friction are lessened. Having the first aperture at the aforementioned junction or in the second tubing creates a likelihood of undesired flexure (e.g., kinking or bunching) as there will be at least some portion of the more flexible second tubing unsupported by a wire guide, and therefore lacking column strength. Not only may such undesired flexure injure an endovascular or other lumen housing the catheter, but it may close off an inflation lumen or other lumen of the catheter, which is undesirable.

BRIEF SUMMARY

The present invention provides a catheter, adaptable for use in endovascular lumens, biliary lumens, or other body lumens, that has a uniform material construction for a substantial portion of its shaft length and that is adaptable for use in a short-wire or long-wire configuration. The problems of increased cost of assembly and various mechanical problems presented by constructing and using a catheter having both semi-flexible hypotube and more flexible second tubing portions of the same catheter are addressed in the present invention. The embodiments described and claimed herein provide a catheter having good pushability and trackability. In one aspect the embodiments described herein also provide a superior catheter shaft having consistent construction material throughout most of the length of the catheter shaft with gradual transition from a stiffer proximal end to a more flexible distal end and lacking sharp transitions that undermine structural integrity. The embodiments herein are also adaptable for use in a variety of minimally invasive surgical treatments (including, e.g., angioplasty or bile duct dilation).

In particular, the present invention includes embodiments of a catheter device comprising an elongate tubular shaft having a consistent material composition for substantially all of its length. The tubular shaft includes a proximal shaft portion having a first flexibility and a distal shaft portion having a second flexibility, wherein the second flexibility is greater than the first flexibility and wherein at least the distal shaft portion comprises at least one score in a surface thereof.

In another aspect, the invention includes a catheter device, which has an elongate tubular shaft having a consistent material composition for substantially all of its length, and a first lumen extending through at least a portion of the tubular shaft. The elongate tubular shaft includes a proximal shaft portion having a first flexibility and a distal shaft portion having a second flexibility, wherein the second flexibility is greater than the first flexibility and wherein at least the distal shaft portion comprises at least one score in a surface thereof and a distal end.

BRIEF DESCRIPTION OF THE DRAWINGS

FIG. 2 is a perspective view of a third catheter shaft with a sleeve;

FIG. 3A is a perspective view of a fourth catheter device having a distal extension and an inflation balloon, with an enlarged detail view of the features at the catheter's distal end;

FIG. 3B is a perspective view of a fifth catheter device with an inflation balloon and an expandable stent;

DETAILED DESCRIPTION

The presently described embodiments of a scored catheter shaft are adaptable for use in a variety of minimally invasive surgical applications (e.g. endoscopic procedures, angioplasty).

Figure 1A:
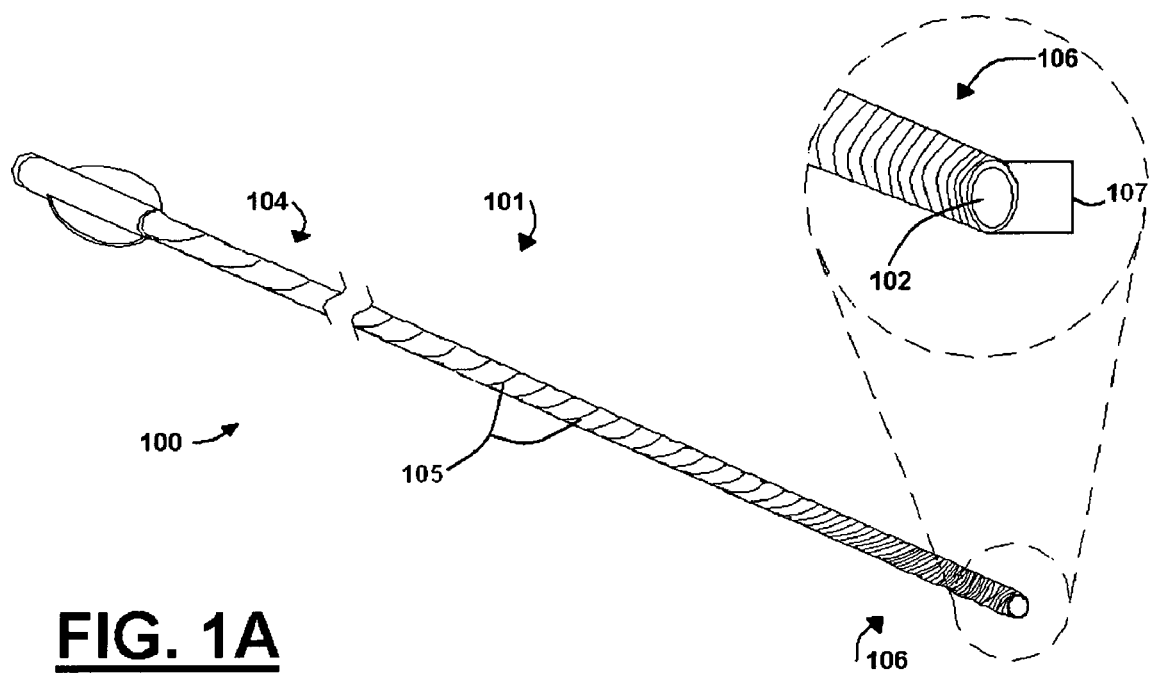
FIG. 1A is a perspective view of a first catheter device, with an enlarged detail view of the catheter's distal end.
Figure 1B:
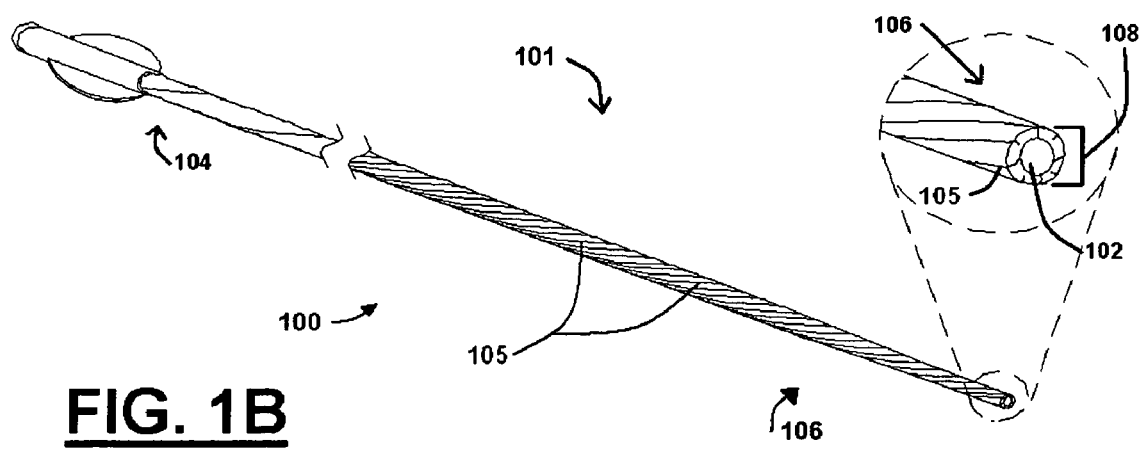
FIG. 1B is a perspective view of a second tapered catheter device, with an enlarged detail view of the catheter's distal end.

FIGS. 1A-1B illustrate an embodiment of a catheter device 100 with a shaft 101 constructed of a stainless steel hypotube material and having an internal lumen 102. The shaft is scored in a helical fashion 105, and the pitch between the helices decreases from the proximal end 104 toward the distal end 106. In this embodiment, the scoring 105 is a surface scoring of the catheter shaft 101. In alternative embodiments, at least some of the scoring may go completely through the wall of the shaft 101. During manufacture of the shaft 101, the scoring may be done using a laser or other appropriate cutting device. Likewise, those of skill in the art will appreciate that in alternative embodiments the tubing material may include a nickel-titanium alloy or other suitable materials.

In the embodiment illustrated in FIG. 1A, the exterior diameter 107 is substantially consistent along the length of the shaft 101. In the embodiment shown in FIG. 1B, the proximal end 104 has a greater exterior diameter than the distal end 106. The catheter shaft 101 tapers toward a smaller exterior diameter 108 along the distal end 106. Tapering can enhance flexibility of the shaft 101 in several ways. For example, flexibility is enhanced by decreasing the outside diameter of the catheter shaft 101 as shown in FIG. 1A. The portion of the catheter shaft 101 having a smaller diameter is more flexible than the portion having a larger diameter. Such tapering also decreases the thickness of the wall of the catheter shaft 101 by tapering the outside diameter while maintaining a substantially consistent interior diameter. Alternatively, tapering may be used within the internal diameter of a catheter, enhancing flexibility by decreasing wall thickness without altering the exterior diameter of the shaft 101. In yet other alternative embodiments, the wall thickness may be substantially constant along the shaft length, with both the inside and outside diameters being tapered. The desired steepness and location of the tapering is determined by the desired size and flexibility needed for a particular application of the catheter shaft 101.

For example, in alternative embodiments, there may be multiple stepwise or gradual differences in diameter to confer different degrees of flexibility throughout the length of the catheter. For example, a catheter shaft 101 for use in coronary arteries will typically benefit from a smaller diameter than a catheter shaft 101 for use in a bile duct, both for gross size and flexibility. A grinding process or other suitable process is used to reduce the exterior diameter as appropriate for the desired application. The flexibility of the catheter shaft 101 may also be altered by using a different construction material composition (e.g., a nickel-titanium alloy or a polymer). In the embodiment shown in the FIG. 1B, the scoring 105 includes a plurality of parallel helices along the distal end 106. As can be seen in the enlarged detail portion of FIG. 1B, some of the helical scores 105 extend through the wall of the catheter shaft. Those of skill in the art will appreciate that the shaft flexibility may be increased or decreased by altering the pitch of the scoring, without significantly altering the internal and/or external diameter of the shaft.

A further embodiment of the catheter shaft 101 includes a coating on internal and/or external surfaces for at least a portion of the catheter shaft 101. The coating is selected to confer or improve one or more properties of reduced friction, flexibility, and sealing a lumen 102 of the catheter. Sealing the lumen 102 allows the lumen to be used, for example, for introduction of inflation fluid to a dilation balloon or for introduction of a medicative substance or a radio-opaque contrast fluid.

The coating may be, for example, a sheath or sleeve 202 as illustrated in FIG. 2. In various alternative embodiments, the form of the sheath 202 may comprise, for example, an extruded sleeve, shrink tube, extruded over-jacket, or dip coat. The composition of the sheath 202 may comprise, for example, HDPE, PTFE, PEBA, PET, polyolefin, polyurethane, polyimide, nylon, or another thermoset or thermoplastic material. A PET shrink tube 202 has the advantage of providing an increased stiffness to a smaller diameter catheter shaft 201. On the other hand, a PEBA shrink tube 202 can be used with a larger diameter catheter shaft 201 where greater flexibility is desired. The type of sleeve 202 material may also be selected to complement other catheter components; for example, a nylon sleeve 202 may bond and interact better with a nylon expandable member such as a balloon or basket, and/or with a nylon wire guide lumen. Selection of, for example, coating materials, shaft composition materials, and wall thickness allow manipulation of the catheter shaft's 201 shore hardness to offer the desired functional properties. Likewise, those of skill in the art will recognize that the method of applying a coating (e.g., over-extrusion, dip-coating, melt fusion, heat shrink lamination) may contribute to the desired properties.

A sleeve or sheath 202 may confer different properties upon the shaft 201 in addition to varied hardness. For example, in the illustrated embodiment of the shaft 201 where scoring 205 extends through the shaft wall to a lumen 207, the sheath 202 allows the lumen to be used for introducing a fluid (e.g., inflation fluid or contrast fluid) by preventing leakage along the scoring 205 in the shaft 201. The fluid-introduction functionality is useful in embodiments where the sheath 202 is disposed on the exterior of the shaft 201 and in other embodiments where the sheath 202 is disposed inside (e.g., lining) the lumen 207 inside the shaft 201. In embodiments where the sheath 202 is on the exterior of the shaft 201, the sheath 202 may decrease the surface friction generated when the shaft 201 is advanced through a passage (e.g. the working lumen of an endoscope, or an endovascular lumen).

FIGS. 3A-3B illustrate embodiments of balloon catheters 300 each comprising a catheter shaft 301. In the embodiment of FIG. 3A, the catheter shaft 301 has an inflation balloon 304 mounted to a distal extension 302. As can clearly be seen in the detail illustration portion of FIG. 3A, the extension 302 houses an inflation lumen 306 which continues from the inflation lumen 306 of the catheter shaft 301. The extension 302 also encloses a wire guide lumen 308. In the illustrated long wire configuration catheter 300, the wire guide lumen 308 extends from the proximal portion of the catheter shaft 301 and extends through the inflation balloon 304 at the distal end of the shaft 301.

The embodiment illustrated in FIG. 3B has an inflation balloon 304 disposed on the distal portion of the catheter shaft 301. An inflation lumen 306 of the catheter shaft 301 opens into the inflation balloon 304. A wire guide lumen 308 traverses the interior of the balloon 304, continuing an open passage of the wire guide lumen 308 of the catheter shaft 301 to a point distal of the inflation balloon 304. An expandable stent 312 is positioned about the balloon 304. In an alternative embodiment, an expandable member other than a balloon (e.g., a basket) is disposed near the distal end of the catheter shaft 301. Such an embodiment optionally may have a wire guide extending through the expandable member. At its proximal end the catheter 300 has a port 310 in fluid communication with the inflation lumen 306. In an alternative embodiment, the port 310 offers access to the guide wire lumen 308. The port 310 may be included in other embodiments, and in other positions on the catheter 300. In another alternative embodiment, the catheter shaft 301 has two ports offering separate access to each of the inflation lumen 306 and the wire guide lumen 308. In other alternative embodiments, the port 310 is useful for introducing another fluid such as a radio-opaque contrast fluid.

Figure 4A:
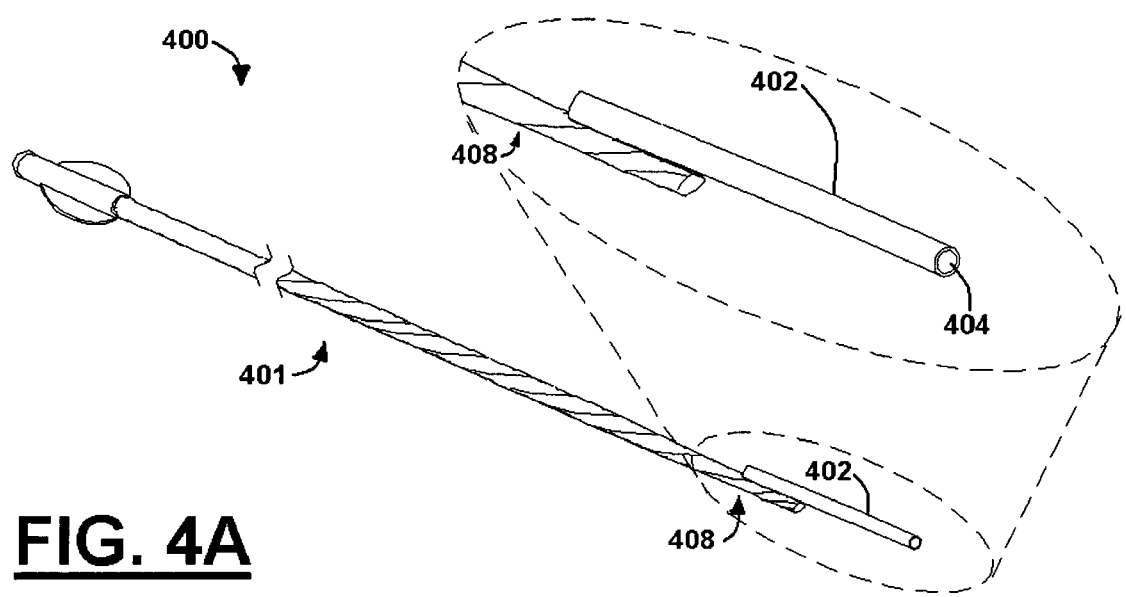
FIG. 4A is a perspective view of a sixth catheter device having an external distal wire guide lumen structure, with an enlarged detail view of the features at the catheter's distal end.
Figure 4B:
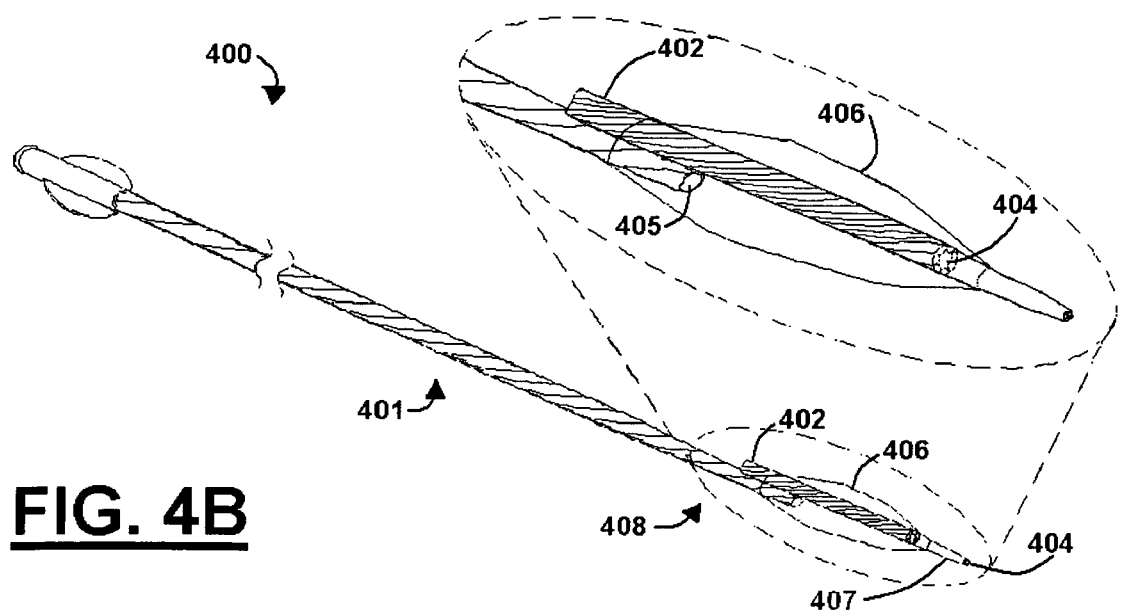
FIG. 4B is a perspective view of a seventh catheter device having an external distal wire guide lumen structure and an inflation balloon, with an enlarged detail view of the features at the catheter's distal end.

FIGS. 4A-4B illustrate embodiments of a catheter device 400 with a polymer shaft 401 having an external, distally disposed short wire guide lumen structure in the form of a cannula 402 having a wire guide lumen 404 disposed therethrough. The polymer shaft can be some other composition in alternative embodiments (e.g., hypotube). In FIG. 4A, the cannula 402 is attached on the distal end 408 of the catheter shaft 401 using an adhesive. Alternative means of attachment include, for example, forced convection heating, radio frequency heating, ultrasonic welding, and laser bonding. Alternatively, shrink tubing may be used as a manufacturing aid to help compress and fuse the cannula 402 to the catheter shaft 401. The shrink tubing may be removed and disposed of after the cannula 402 is connected to the catheter shaft 401, or may remain on as part of the connected structure. If the catheter shaft 401 has a coating, the cannula 402 may be bonded to the coating or directly to the catheter shaft 401. In the embodiment shown in FIG. 4B, the cannula 402 is constructed of multifilar tubing. An inflation balloon 406 is mounted on the distal end 408 of the catheter shaft 401. An inflation lumen 405 of the catheter shaft 401 is open to the interior of the inflation balloon 406. The cannula 402 extends through the inflation balloon 406 and has an extension 407 on its distal end. A wire guide lumen 404 runs through the length of the cannula 402 and the extension 407.

Figure 4C:
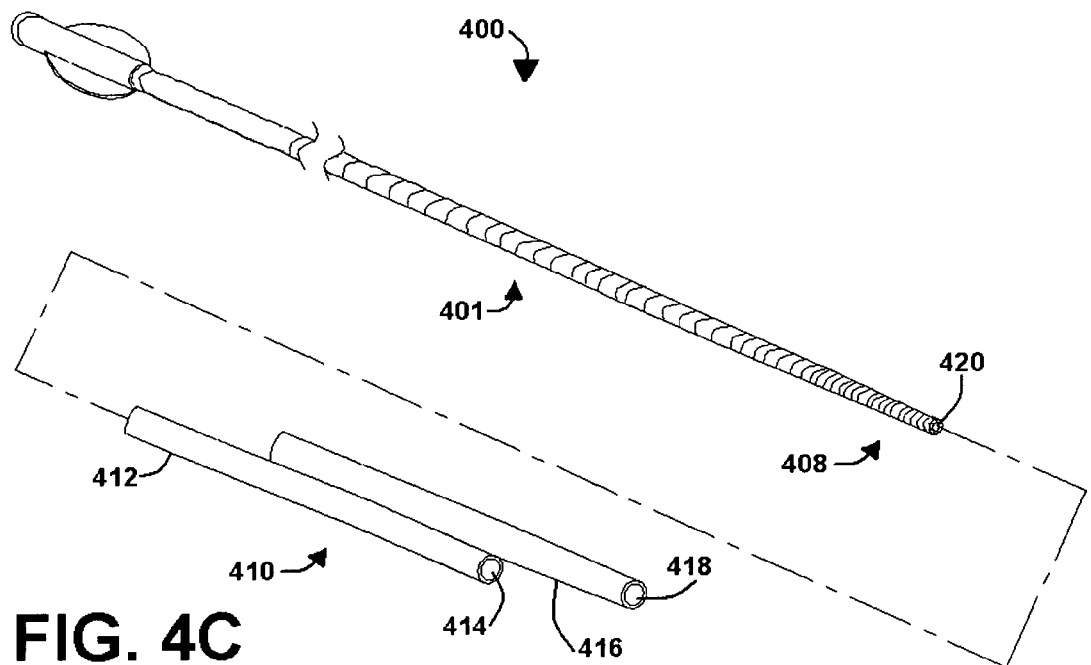
FIG. 4C is a perspective view of an eighth catheter device with a distal dual lumen structure having a wire guide lumen structure and a mounting portion.

In FIG. 4C, the shaft 401 of the catheter device 400 is scored in a series of circumferential rings that are nearer each other along the distal-most part of the distal end 408 than along a more proximal part of the distal end 408. There is no scoring on a substantial part of the proximal portion. This alternative embodiment of a scoring configuration provides a more flexible distal portion and a less flexible proximal portion, conferring the variance in desired stiffness as described above. A dual lumen structure 410 is disposed on the distal end 408 of the catheter shaft 401. A portion of the length of dual lumen structure 410 has a "FIG. 8" cross section. A mounting portion 412 of the dual lumen structure 410 has a lumen 414. The distal end 408 of the catheter shaft 401 fits into the lumen 414. The lumen 414 may be completely occupied by the distal end 408 of the catheter shaft 401, or it may continue coaxially beyond the distal end 408 so as to form an extension in fluid communication with a lumen 420 in the shaft 401. A wire guide portion 416 of the dual lumen structure 410 has a wire guide lumen 418 running therethrough. The dual lumen structure 410 is attached on the distal end 408 of the catheter shaft 401 using one of the attachment methods described for the embodiment shown in FIG. 4A. In this embodiment, the lumen 414 of the dual lumen structure is in fluid communication with a lumen 404 of the catheter shaft 401. In an alternative embodiment, a part of the mounting portion 412 is mounted inside the lumen 420 of the catheter shaft 401.

Figure 5A:
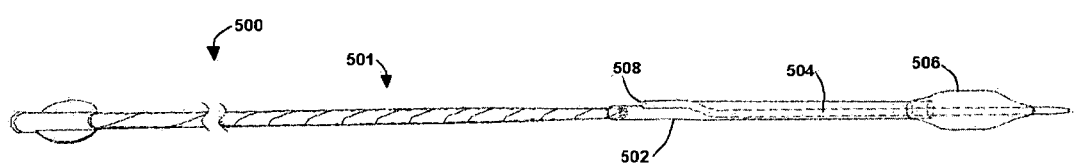
FIGS. 5A-5B show a side view of ninth and tenth catheter devices having a distal extension and a wire guide lumen structure.
Figure 5B:
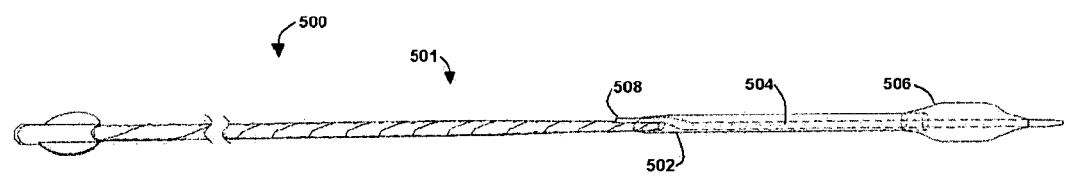
Figure 5C:
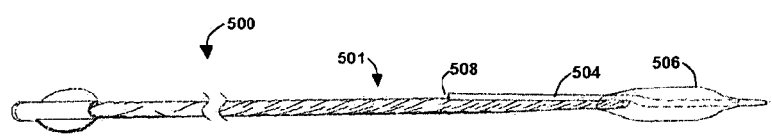
FIG. 5C is a side view of an eleventh catheter device having an external distal wire guide lumen structure and an inflation balloon.

FIGS. 5A-5C illustrate embodiments of a balloon catheter device 500 with a shaft 501 having a short wire guide configuration. The embodiments shown in FIGS. 5A-5B each have a coaxial extension 502 of the catheter shaft 501, a short wire guide lumen structure in the form of a tube 504, and an inflation balloon 506. In the embodiment illustrated in FIG. 5A, the proximal end 508 of the tube 504 is disposed distal of the juncture of the extension 502 with the catheter shaft 501. The tube 504 enters the extension 502 and extends through the distal end of the balloon 506. In the embodiment illustrated in FIG. 5B, the proximal end 508 of the tube 504 is disposed proximal of the juncture of the extension 502 with the catheter shaft 501. The tube 504 enters the extension 502 and extends through the distal end of the balloon 506.

The embodiment illustrated in FIG. 5C does not have an extension. The balloon 506 is disposed on a distal portion of the catheter shaft 501. The proximal end 508 of the tube 504 is disposed proximal of the juncture of the extension 502 with the catheter shaft 501 and is affixed to the exterior of the catheter shaft 501. The tube 504 passes through the middle of the balloon 506 and extends through the distal end of the balloon 506. The shaft 501 in the embodiment of FIG. 5C is scored in a combination of semi-circles, semi-ellipses, spirals, and semi-spirals. In alternative embodiments, each of these scoring patterns may be used alone, in combination with each other, or with a helical scoring pattern.

In each of the embodiments shown in FIGS. 5A-5C, the placement of the proximal end 508 of the tube 504 along the catheter shaft 501 affects the flexibility of the shaft 501. Therefore, variation in the placement is useful in increasing or reducing flexibility as desired in these and other embodiments.

Figure 6:
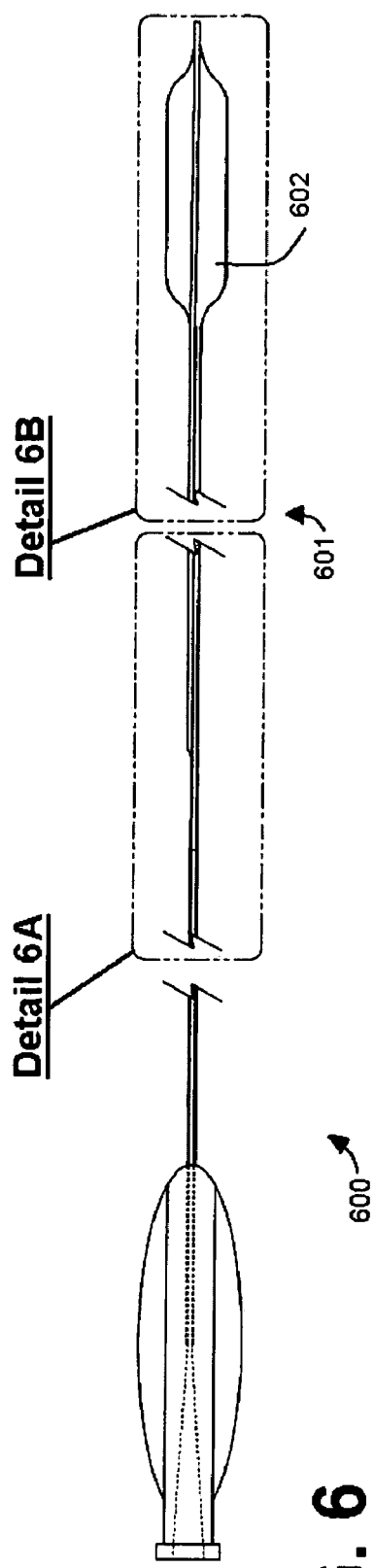
FIG. 6 is a side view of a twelfth tapered catheter device having an external distal wire guide lumen structure and an inflation balloon.
Figure 6A:
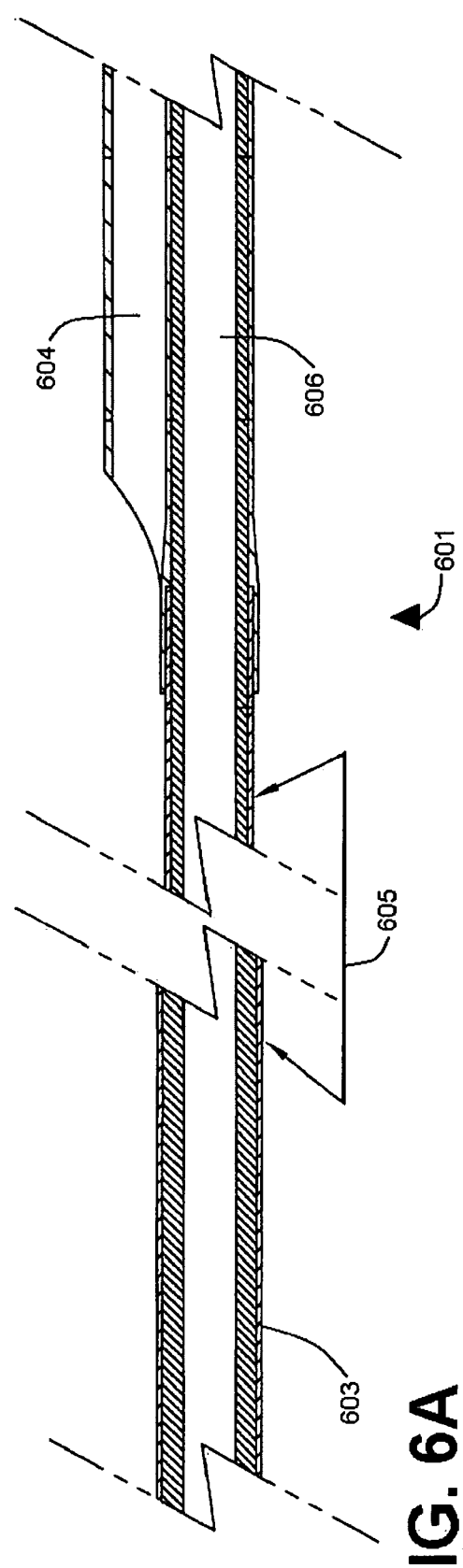
FIG. 6A is a detail of FIG. 6 and shows a longitudinal cross-sectional view of the tapering portion and external wire guide lumen of the twelfth catheter device.

FIG. 6 illustrates one embodiment of a balloon catheter 600 having an elongate shaft 601. An inflation balloon 602 is disposed near the distal end. FIG. 6A is an enlarged detail illustration of a middle section of the balloon catheter 600. As shown in FIG. 6A, the shaft 601 includes an external wire guide lumen structure 604 and an internal inflation lumen 606. As shown in FIG. 6A, the catheter shaft 601 is coated with a PEBA coating 603. The coating 603 serves to reduce friction during introduction of the catheter shaft 601 and provides a seal to prevent leakage of inflation fluid from the inflation lumen 606 through the walls of the shaft 601. As can also be seen in FIG. 6A, the catheter shaft 601 tapers distally to a smaller diameter along the region 605. In an alternative embodiment, a second internal lumen in addition to the inflation lumen 606 allows introduction of a fluid (e.g. contrast fluid).

Figures 6B, 6C, 6D:
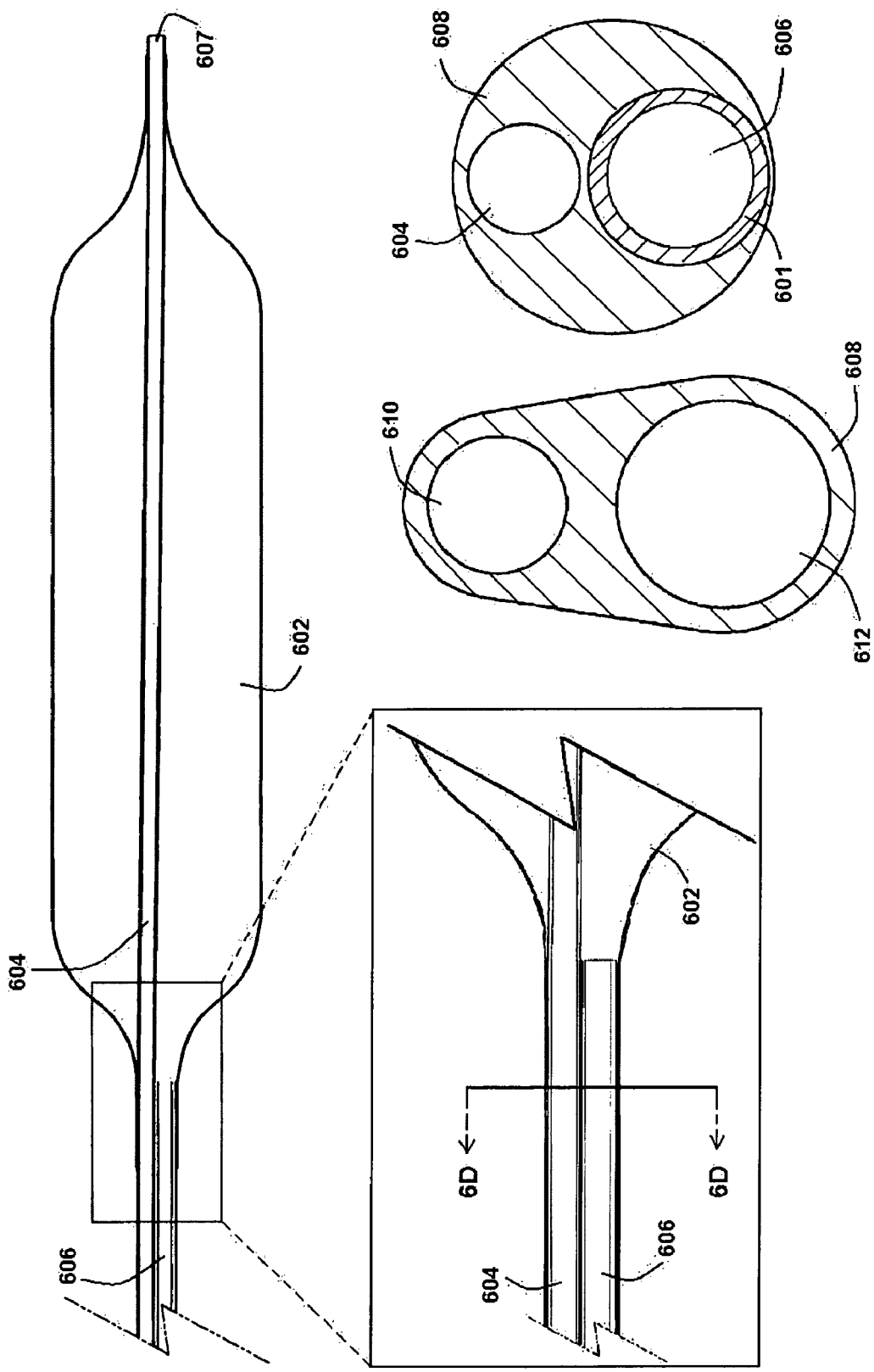
FIG. 6B is a detail of FIG. 6 and shows a longitudinal cross-sectional view of the distal portion of the twelfth catheter device, with an enlarged detail view of features where the catheter shaft meets the balloon.
FIG. 6C is a transverse cross-sectional view of a dual-lumen mounting sleeve.
FIG. 6D is a transverse cross-sectional view along line 6D-6D of FIG. 6B showing two lumens of the twelfth catheter device surrounded by a dual-lumen mounting sleeve.

FIG. 6B is an enlarged detail illustration of a distal section of the balloon catheter 600. As shown in FIG. 6B, the inflation lumen 606 opens into the inflation balloon 602, and the wire guide lumen 604 extends through the balloon 602 to the distal end 607. FIG. 6B includes an enlarged detail portion more clearly illustrating the relationship between the balloon 602 and the two lumens (604 and 606). In this embodiment, the balloon 602 and wire guide lumen 604 are mounted to the shaft 601 with a PEBA shrink sleeve 608. As shown in FIG. 6C, a cross-sectional view of the sleeve 608 has approximately a figure-eight shape before mounting. The sleeve 608 has two central apertures (610 and 612) to allow mounting the sleeve 608 over the wire guide lumen 604 and the shaft. In this embodiment, after the balloon 602 and wire guide 604 are assembled to the shaft 601 together with the sleeve 608, the sleeve 608 is heated to shrink and form to the assembly of shaft 601, balloon 602, and wire guide 604. FIG. 6D is a transverse cross section along line 6D-6D of FIG. 6B, and shows the finished configuration. The sleeve 608 forms to the shaft 601 and leaves open the inflation lumen 606 and the wire guide lumen 604. In alternative embodiments, the shaft coating (if any) may be a material other than PEBA, and may be the same or different than the material in a mounting sleeve used to mount a balloon.

It is therefore intended that the foregoing detailed description be regarded as illustrative rather than limiting, and that it be understood that it is the following claims, including all equivalents, that are intended to define the spirit and scope of this invention.

I claim:

1. A catheter device comprising:
an elongate tubular shaft having a consistent metallic material composition for substantially all of its length, said elongate tubular shaft comprising
a first lumen extending through at least a portion of the tubular shaft;
a proximal shaft portion having a first flexibility;
a distal shaft portion having a second flexibility;
wherein the second flexibility is greater than the first flexibility and wherein at least the distal shaft portion comprises
at least one score in a surface thereof, and
a distal end region;

an inflation balloon disposed upon the distal end region of the scored shaft, wherein a portion of the distal end region extends into and terminates within a lumen of the inflation balloon, thereby providing fluid communication between the first lumen and the balloon lumen; and a wire guide tube wholly external to the shaft and disposed substantially parallel to the first lumen along the shaft distal end region, where the wire guide tube extends beyond a distal shaft end lengthwise through the balloon lumen, providing a patent path of mechanical communication therethrough, and a lumen of the wire guide tube is open through a distal balloon end; and wherein an attachment of the wire guide tube to the shaft comprises a figure-eight-shaped heat-shrink polymer sleeve.

2. The catheter device of claim 1 wherein the at least one score extends along a length of the distal shaft portion in a helical fashion, thereby forming at least one helical score.

3. The catheter device of claim 2, wherein the at least one helical score comprises a variable pitch.

4. The catheter device of claim 3, wherein the pitch of the helical score along a more distal portion of the elongate tubular shaft is less than the pitch of the helical score along a less distal portion of the elongate tubular shaft.

5. The catheter device of claim 1, wherein the elongate tubular shaft comprises a shaft wall and the at least one score extends completely through at least a portion of the shaft wall.

6. The catheter device of claim 5, wherein the shaft wall of the proximal shaft portion comprises a first wall thickness that is greater than a second wall thickness of the shaft wall of the distal shaft section.

7. The catheter device of claim 1, wherein the at least one score comprises a plurality of generally helical scores.

8. The catheter device of claim 7, wherein the plurality of scores along a less distal portion of the shaft has a first spacing that is greater than a second spacing of the plurality of scores along a more distal portion of the shaft.

9. The catheter device of claim 7, wherein at least one score of the plurality of scores forms at least one circumferential score around the shaft.

10. The catheter device of claim 1, further comprising a sleeve coating at least a portion of the tubular shaft.

11. The catheter device of claim 1, further comprising a balloon-deployable stent.

12. The catheter device of claim 1, wherein the first lumen is configured for passage of a fluid.

13. A catheter device comprising:

an elongate tubular shaft having a consistent metallic material composition for substantially all of its length, a proximal shaft portion having a first flexibility, and a distal shaft portion having a second flexibility, wherein the second flexibility is greater than the first flexibility, and wherein at least the distal shaft portion comprises at least one helical score in a surface thereof;

a wire guide lumen structure attached to and wholly external of the distal shaft portion, the attachment comprising a figure-eight-shaped heat-shrink polymer sleeve; and an expandable balloon structure attached directly to the distal shaft portion of the scored shaft such that a portion of the distal end region extends into and terminates within a lumen of the expandable balloon structure, further where the wire guide lumen structure extends lengthwise beyond the distal shaft end region through the balloon lumen, providing a patent path of mechanical communication therethrough, and a lumen of the wire guide lumen structure is open through a distal balloon end.

\* \* \* \* \*